US008540624B2

(12) United States Patent
Bissinger

(10) Patent No.: US 8,540,624 B2
(45) Date of Patent: Sep. 24, 2013

(54) INSTRUMENT FOR ENDOSCOPIC SURGERY

(75) Inventor: Matthias Bissinger, Emmendingen (DE)

(73) Assignee: Guenter Bissinger Medizintechnik GmbH, Teningen (DE)

(*) Notice: Subject to any disclaimer, the term of this patent is extended or adjusted under 35 U.S.C. 154(b) by 268 days.

(21) Appl. No.: 12/807,749

(22) Filed: Sep. 13, 2010

(65) Prior Publication Data
US 2011/0065992 A1 Mar. 17, 2011

(30) Foreign Application Priority Data
Sep. 11, 2009 (DE) .......................... 10 2009 040 960

(51) Int. Cl.
*A61B 1/00* (2006.01)
(52) U.S. Cl.
USPC ................................ 600/131; 600/101; 606/1
(58) Field of Classification Search
USPC ................. 600/101, 104–107, 114, 130, 131; 606/1
See application file for complete search history.

(56) References Cited

U.S. PATENT DOCUMENTS

| 4,655,216 A * | 4/1987 | Tischer ............................ 606/51 |
| 5,322,055 A * | 6/1994 | Davison et al. .................... 601/2 |
| 5,411,519 A * | 5/1995 | Tovey et al. ..................... 606/207 |
| 5,607,450 A * | 3/1997 | Zvenyatsky et al. ........... 606/206 |
| 5,873,873 A * | 2/1999 | Smith et al. ....................... 606/1 |
| 5,893,835 A * | 4/1999 | Witt et al. .......................... 601/2 |
| 5,980,510 A * | 11/1999 | Tsonton et al. .................... 606/1 |

FOREIGN PATENT DOCUMENTS
DE  101 56 917  6/2003

* cited by examiner

*Primary Examiner* — Ahmed Farah
(74) *Attorney, Agent, or Firm* — Collard & Roe, P.C.

(57) ABSTRACT

An instrument for endoscopic surgery, with a housing having a grip element and a shaft-receiving element, the grip element having a fixed grip part and a pivotable grip part, and the shaft-receiving element being intended to receive and lock the proximal end of a tubular shaft, with a tool at the distal end of the shaft, and with an actuation member extending through the shaft and being longitudinally movable therein, or with a slide piece acting on the actuation member. The actuation member engages in the shaft-receiving element of the housing and is coupled to the grip part mounted pivotably on the housing, so that a pivoting of the grip part causes a longitudinal movement of the actuation member and an actuation of the tool. The grip element of the housing is rotatable relative to the shaft-receiving element of the housing about a rotation axis extending perpendicular to the shaft.

15 Claims, 10 Drawing Sheets

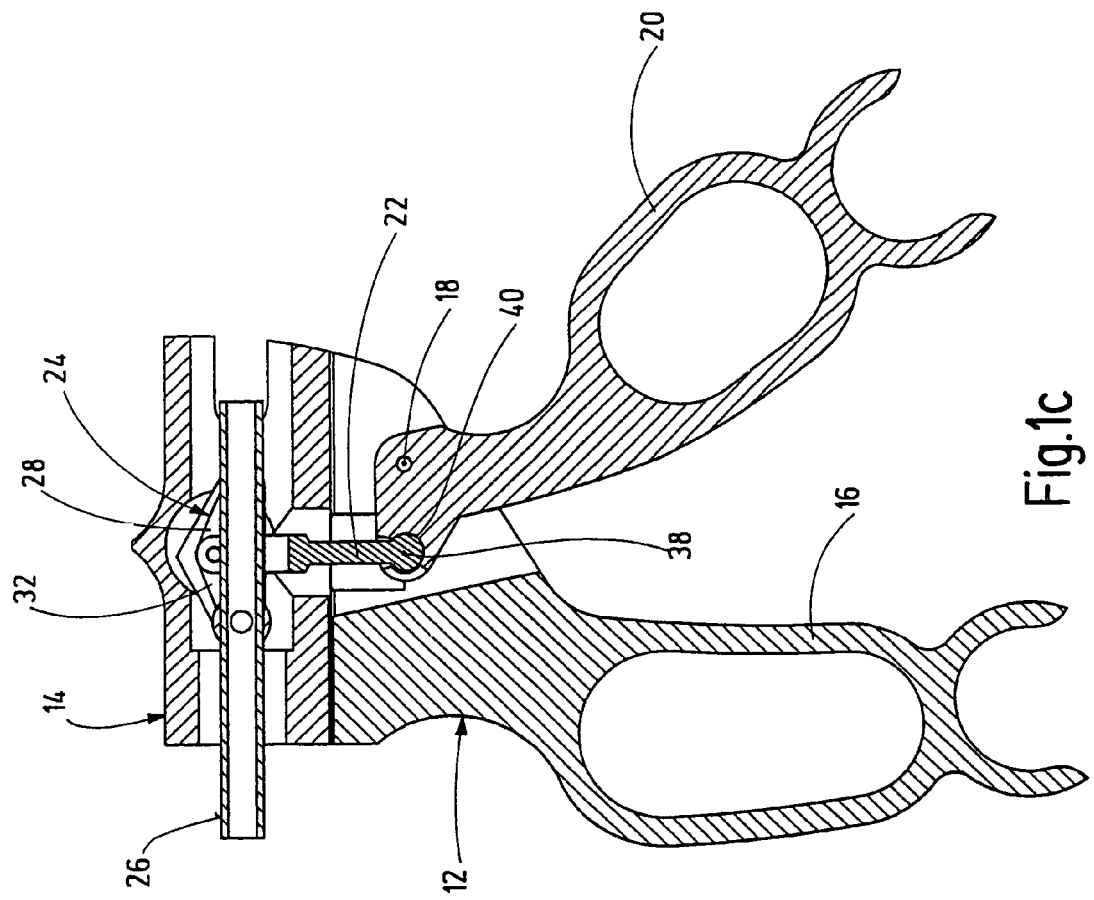
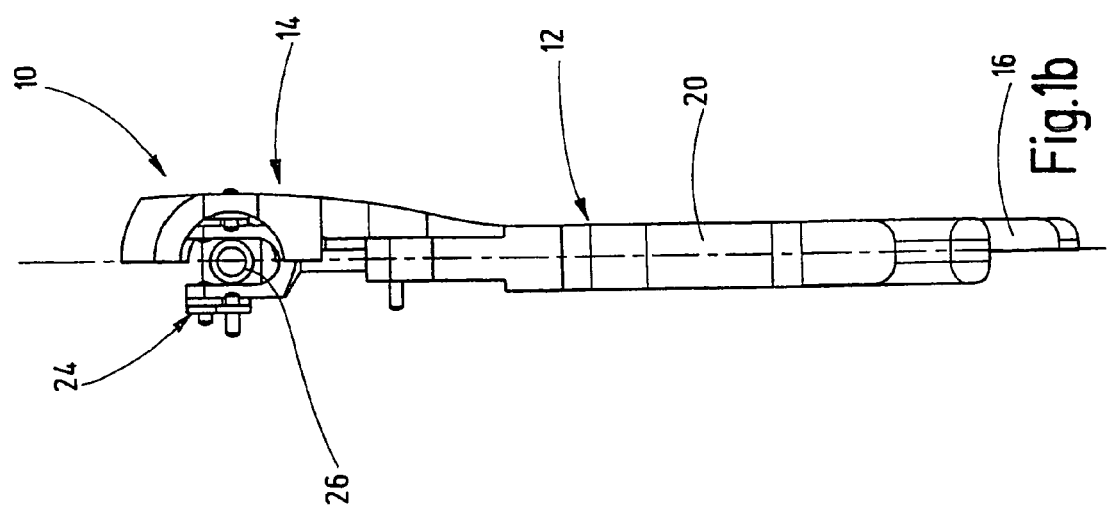

INSTRUMENT FOR ENDOSCOPIC SURGERY

CROSS REFERENCE TO RELATED APPLICATIONS

Applicant claims priority under 35 U.S.C. §119 of German Application No. 10 2009 040 960.2 filed on Sep. 11, 2009, the disclosure of which is incorporated by reference.

BACKGROUND OF THE INVENTION

The invention relates to an instrument for endoscopic surgery, with a housing having a grip element and a shaft-receiving element, the grip element having a fixed grip part and a pivotable grip part, and the shaft-receiving element being intended to receive and lock the proximal end of a tubular shaft, with a tool arranged at the distal end of the shaft, and with an actuation member being provided for the tool and extending through the shaft and being longitudinally movable therein, or with a slide piece acting on the actuation member, the actuation member engaging with its proximal end in the shaft-receiving element of the housing and being able to be coupled there, via a coupling mechanism arranged in the housing, to the grip part mounted pivotably on the housing, in such a way that a pivoting of the grip part causes a longitudinal movement of the actuation member and an actuation of the tool. The invention further relates to a housing for such an instrument.

An instrument of this kind is known, for example, from the earlier application DE 10156917 A1 filed by the Applicant. During the operation performed with such an instrument, the patient generally lies on an operating table and the surgeon stands to the side behind the patient's head, for example. The surgeon will often maneuver two instruments simultaneously, of which at least one will be of the type mentioned above. Depending on the orientation of the shaft, this forces the surgeon to hold and operate the instrument with his hands in an unnatural position, which can lead to early fatigue.

SUMMARY OF THE INVENTION

In light of this problem, the object of the present invention is to make available an instrument of the type mentioned at the outset which permits a natural position of the hands and therefore allows the surgeon to work without experiencing fatigue.

This object is achieved by the combination of features set forth in claim 1. Advantageous developments and refinements of the invention are set forth in the dependent claims.

The invention is based primarily on the recognition that the instrument can be used without causing fatigue if the surgeon's hand can be oriented independently of the orientation of the shaft carrying the tool. Therefore, according to the invention, provision is made that the grip element of the housing is rotatable relative to the shaft-receiving element of the housing about a rotation axis extending perpendicular to the shaft. In this way, the grip element can be rotated relative to the shaft-receiving element into a position that is comfortable for the surgeon, without changing the orientation of the tool.

In a preferred embodiment of the invention, the pivotable grip part has a ball socket in which a ball head of an actuation ram is mounted (rotationally symmetrically). In principle, any other configuration of the actuation ram and of the engagement thereof in the pivotable grip part is also possible where said configuration has a symmetry of rotation with respect to the rotation axis and is fixed in the actuation direction of the ram. The actuation ram should therefore be arranged coaxially with respect to the rotation axis of the grip element relative to the shaft-receiving element.

The actuation ram is expediently coupled to a transmission element for converting the pivoting movement of the pivotable grip part into a sliding movement of the actuation member, and the transmission element is arranged in the shaft-receiving element of the housing.

The transmission element can be constructed in different ways.

In a first preferred variant, the transmission element has substantially the shape of a sector of a circle with a lever extension and is mounted pivotably in the shaft-receiving element, with its axis parallel to the pivotable grip part, and the outer edge of the transmission element is provided at least partially with teeth which cooperate with complementary teeth on the shaft, such that a rack-and-pinion mechanism as it were is created, and the free end of the lever extension is articulated pivotably on the actuation ram.

In another preferred variant, the transmission element has a first pair of connecting rods which are mounted with one end in the shaft-receiving element, on both sides of the shaft, and whose other ends are articulated pivotably on the free ends of an extension provided on the actuation ram and engaging like a fork around the shaft, and a second pair of connecting rods are articulated with one end on the extension of the actuation ram, coaxially with respect to the first pair of connecting rods, and have their other end articulated pivotably on the actuation member.

In a variant that is preferred particularly for instruments permitting electrical coagulation, the transmission element has a substantially L-shaped pivot lever which is mounted along a pivot axis in the shaft-receiving element and which has one arm coupled pivotably to the actuation ram, while its other arm engages like a fork around the slide piece and is coupled pivotably to the latter.

In this case, the slide piece can have, for the purpose of coupling it to the transmission element, two laterally protruding pins which engage in U-shaped recesses in the free ends of the fork-like arm of the transmission element.

Alternatively, for the purpose of coupling it to the transmission element, the slide piece can have, at least in its lateral area, recesses or a peripheral indent in which circular end portions of the fork-like arm of the transmission element engage.

The connection between the shaft-receiving element and the grip element of the housing should not have too easy an action. Therefore, in a preferred embodiment of the invention, a shaft ring or spring ring is arranged, coaxially with respect to the rotation axis, between the grip element and the shaft-receiving element. The spring force of the shaft ring or spring ring determines the force that is needed to rotate the two housing elements and can be chosen in accordance with the intended purpose of use. A locking mechanism is also possible that acts at predetermined angle spacings, for example using a combination of a ball and a locking opening.

If the instrument is provided with a capacity for bipolar coagulation, an electrical alternating voltage can be applied to the tool for electrosurgical treatment of tissue. It is then expedient that electrical contacts for attachment of a voltage source are provided in the proximal area of the slide piece, and the contacts are connected to the tool via lines that are routed in an electrically insulated manner through the shaft.

Since it can be advantageous if the shaft-receiving element and the grip element in a defined position of rotation can be secured against further rotation, provision is made, according to a further embodiment of the invention, that a spring-loaded locking pin is provided in the fixed grip part and is movable, relative to the shaft-receiving element, between a locking position, in which the grip element is not rotatable relative to the shaft-receiving element, and a rotation position, in which the grip element and the shaft-receiving element are rotatable relative to each other. A locking plate lying opposite the locking pin in the fixed grip part is expediently arranged in the shaft-receiving element, into which locking plate the locking pin can lock at predetermined angle spacings.

The housing according to the invention for an instrument for endoscopic surgery, in particular for an instrument of the kind described above, has a grip element and a shaft-receiving element, the grip element having a fixed grip part and a pivotable grip part, and the shaft-receiving element being intended to receive the proximal end of a tubular tool shaft. It is characterized in that the grip element is rotatable relative to the shaft-receiving element about a rotation axis extending perpendicular to the shaft. A shaft ring or spring ring is preferably arranged, coaxially with respect to the rotation axis, between the grip element and the shaft-receiving element and defines the force that is needed for a rotation of the two housing parts relative to each other.

BRIEF DESCRIPTION OF THE DRAWINGS

The invention is explained in more detail below with reference to illustrative embodiments depicted schematically in the drawing, in which:

FIGS. 1a to 1d show a perspective view and various sectional views of the proximal area of a first illustrative embodiment of the instrument;

DETAILED DESCRIPTION OF THE EMBODIMENTS

Figure 2A:
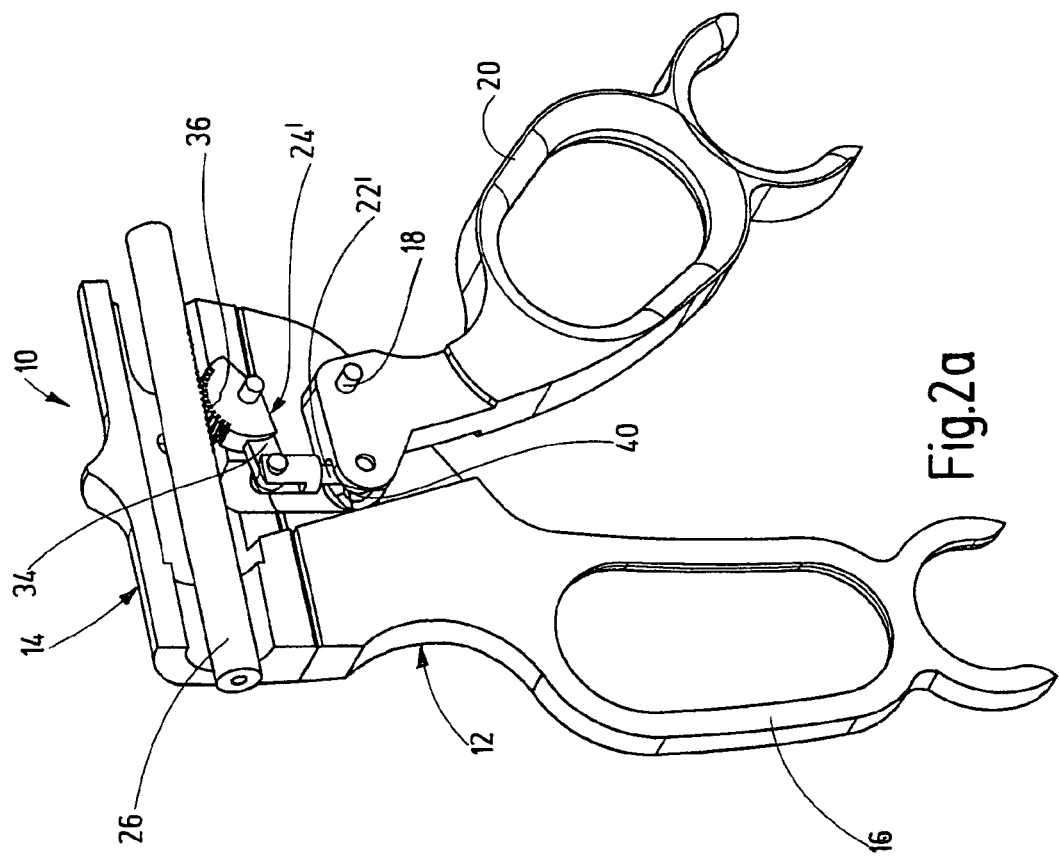
FIGS. 2a to 2d show a perspective view and various sectional views of the proximal area of a second illustrative embodiment of the instrument.

The instrument 10 depicted in the drawing has a housing consisting principally of a grip element 12 and of a shaft-receiving element 14, the grip element 12 being rotatable relative to the shaft-receiving element 14 about an axis extending perpendicular to a shaft axis. The grip element 12 itself has a fixed grip part 16, and a grip part 20 mounted pivotably on the latter about an axis 18. The scissor-like movement of the two grip parts relative to each other is converted, via an actuation ram 22 and a transmission element 24, into an axial movement of the actuation member or slide piece, which leads to an actuation of the tool (not shown), for example a clamp or scissors.

Figure 1A:
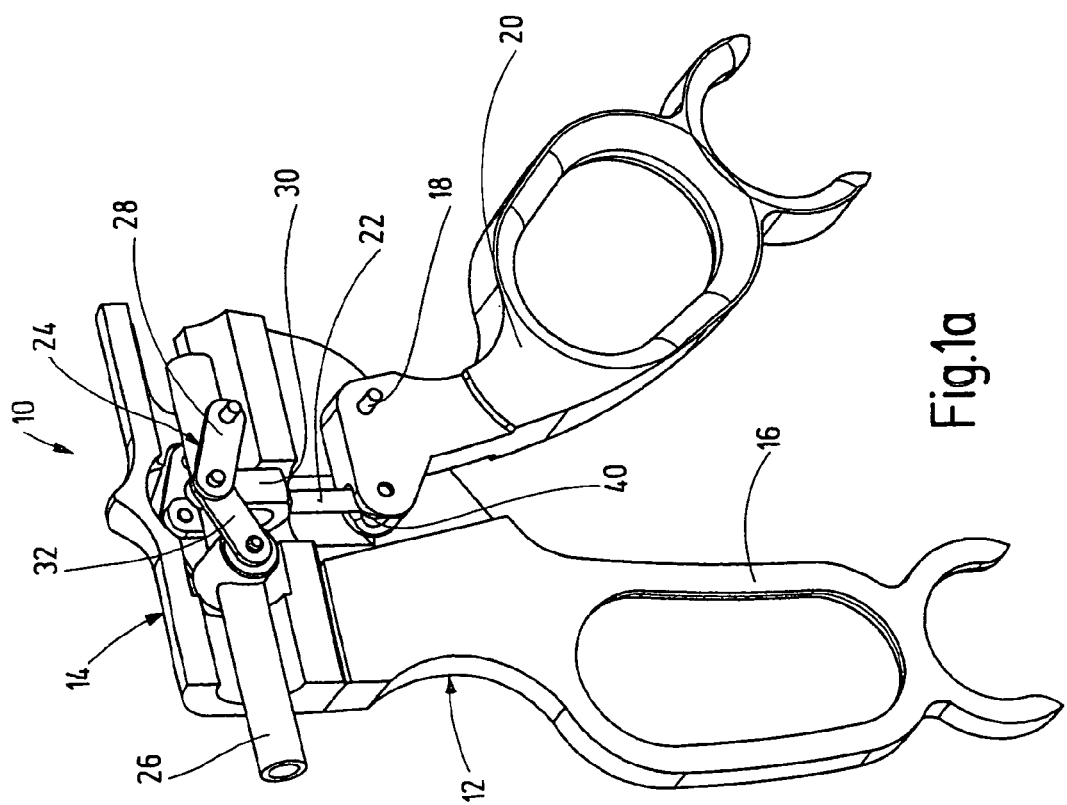
Figure 4D:
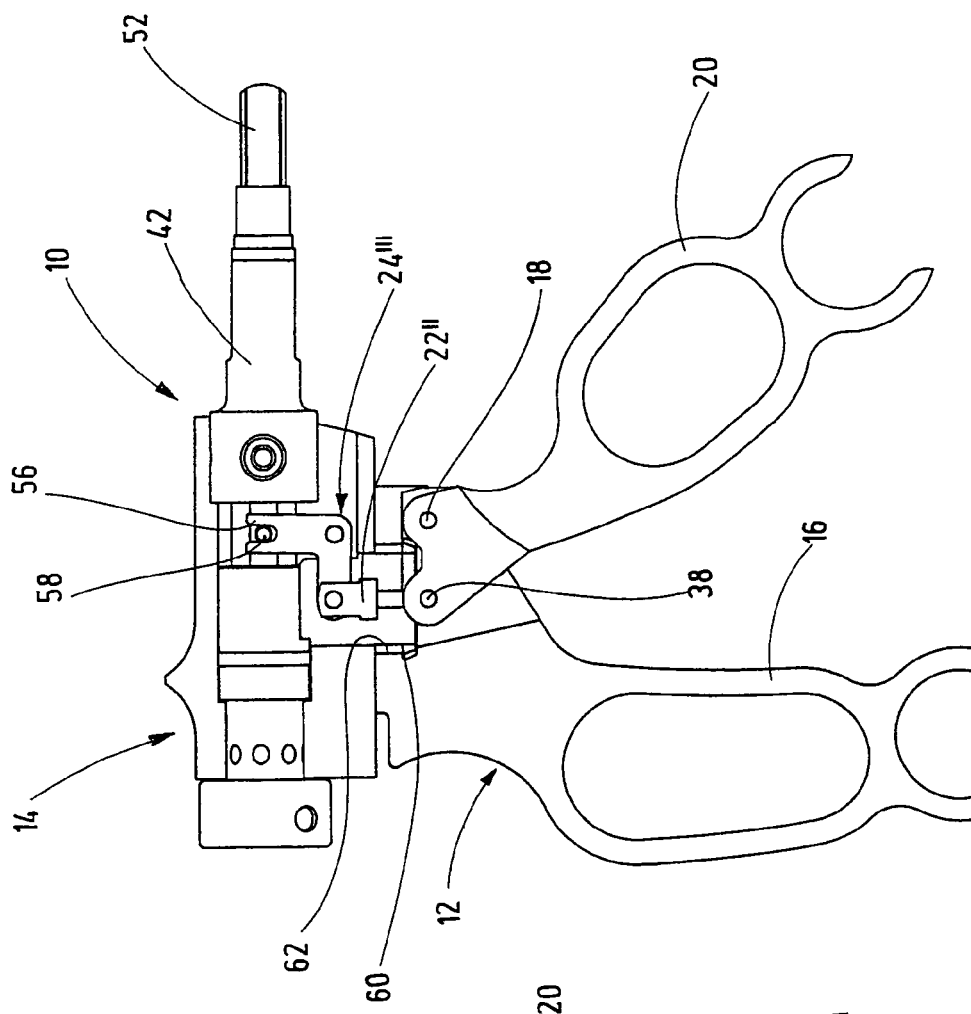
FIGS. 4a to 4d show a perspective view and various sectional views of the proximal area of a fourth illustrative embodiment of the instrument.
Figure 1D:
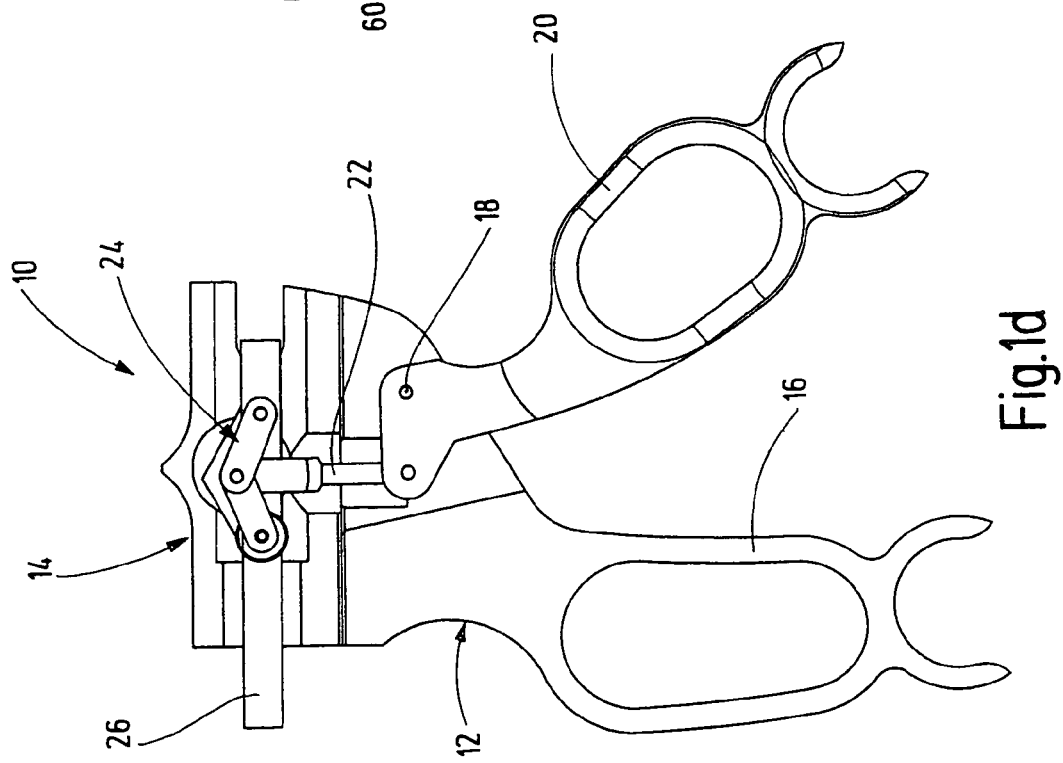
Figure 2C:
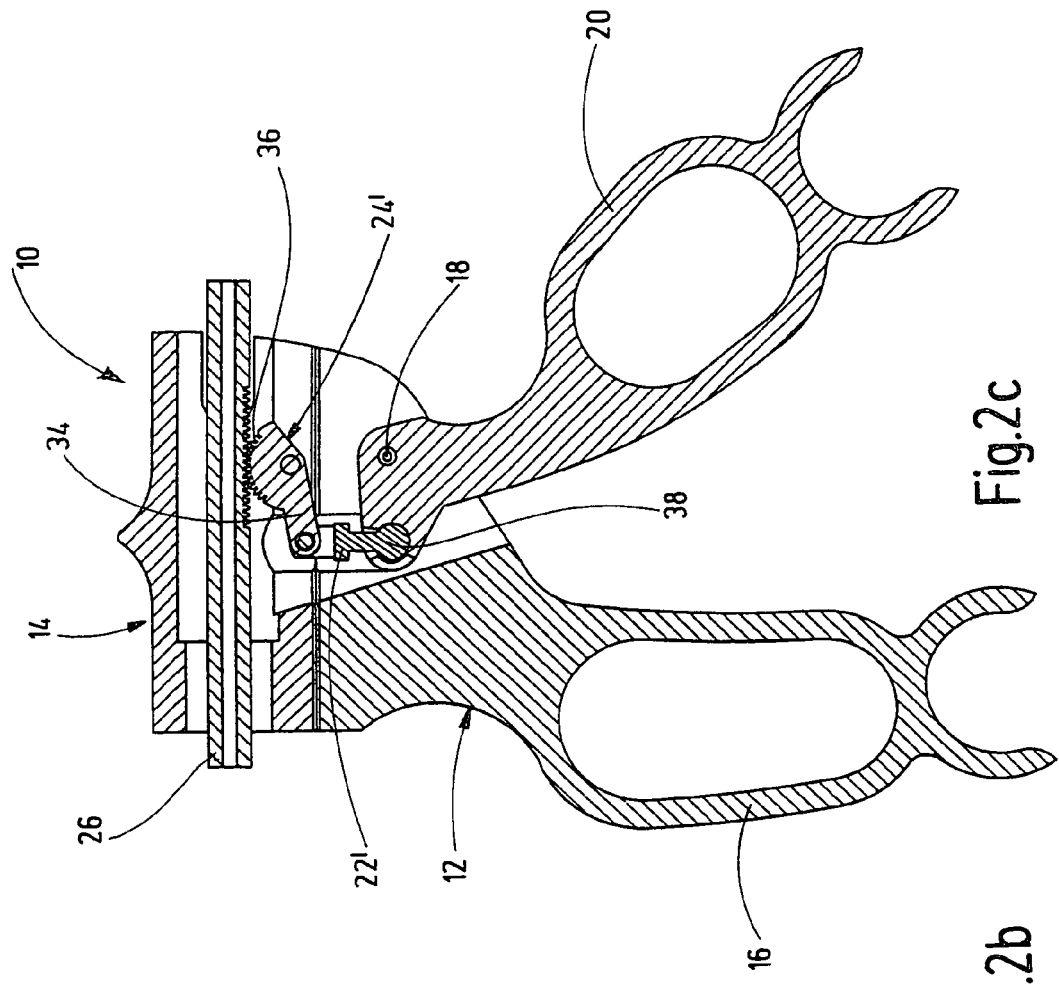
Figure 2B:
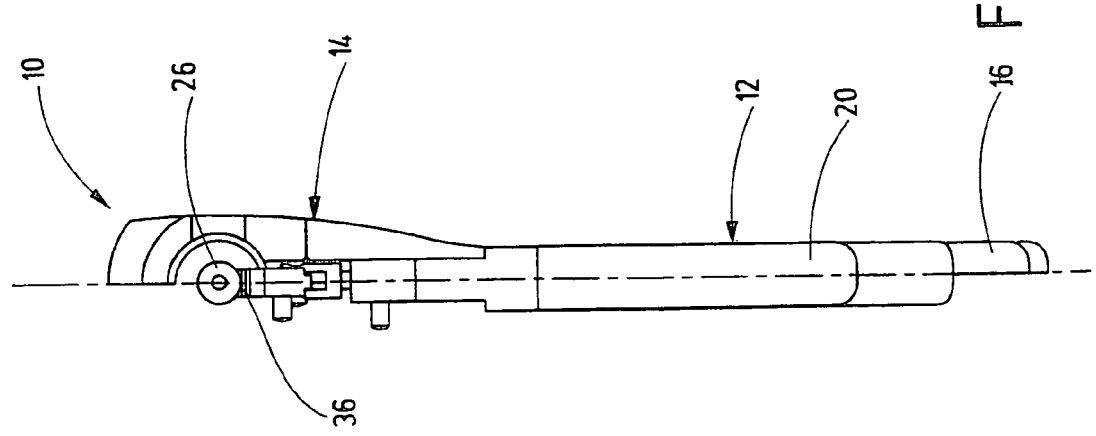
Figure 3A:
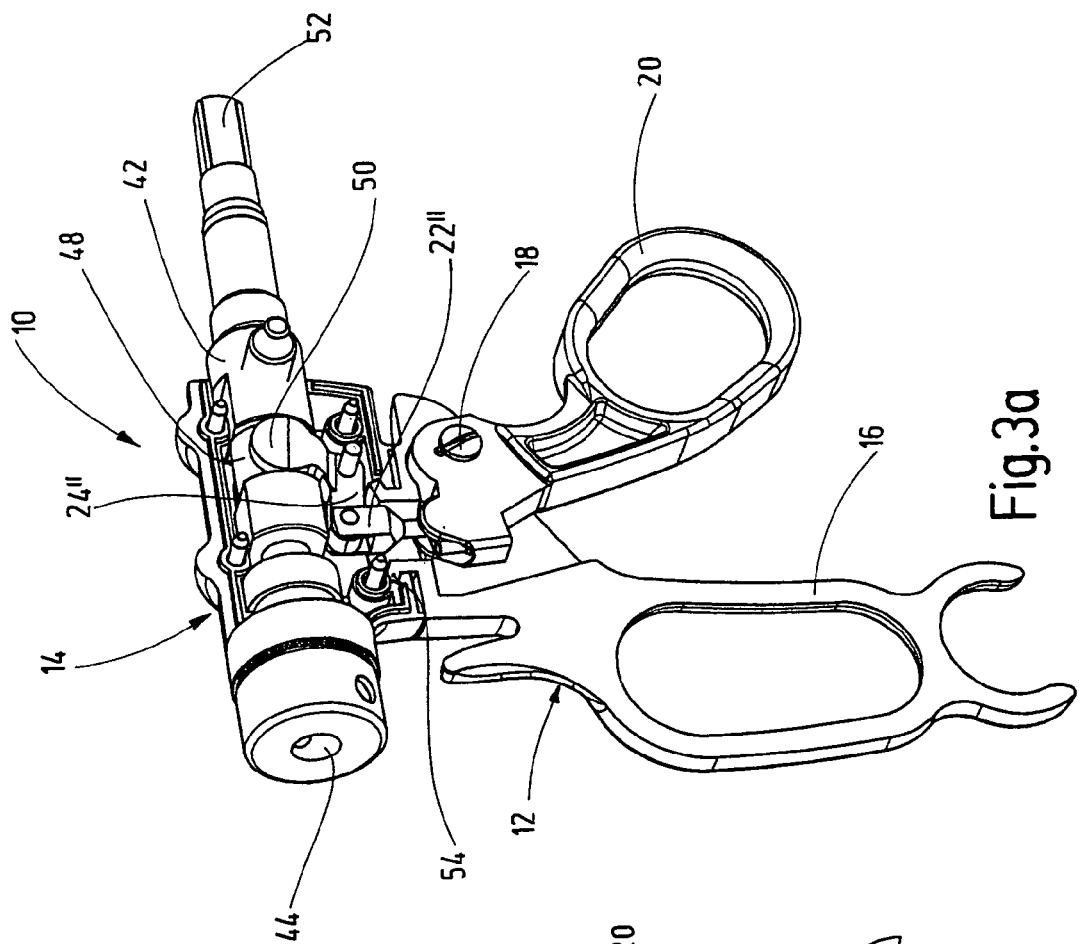
FIGS. 3a to 3d show a perspective view and various sectional views of the proximal area of a third illustrative embodiment of the instrument.
Figure 2D:
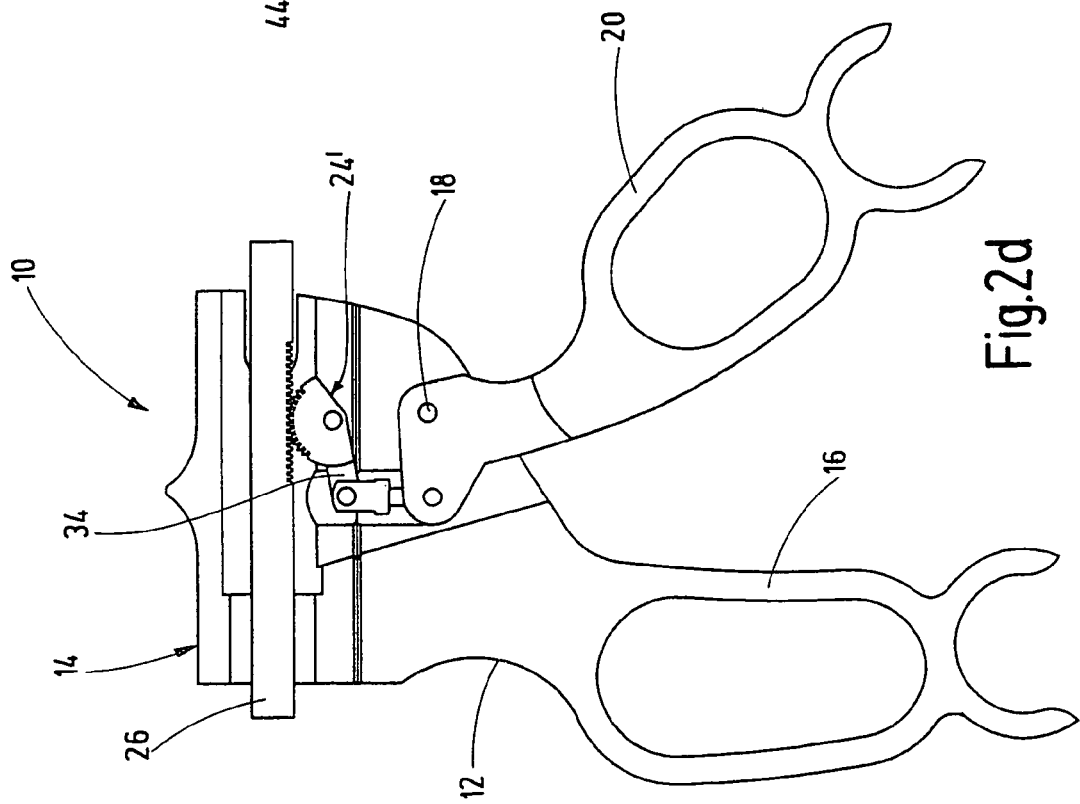
Figure 3C:
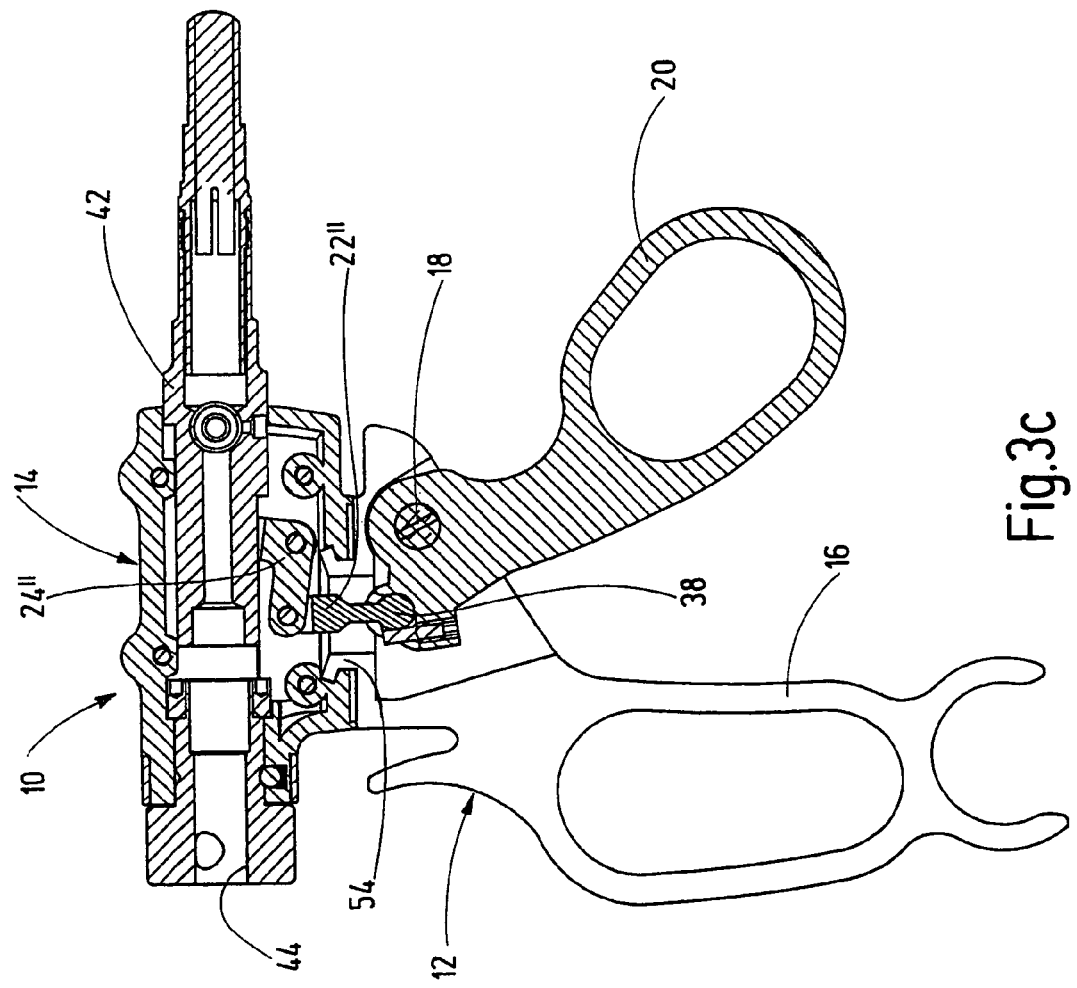
Figure 3B:
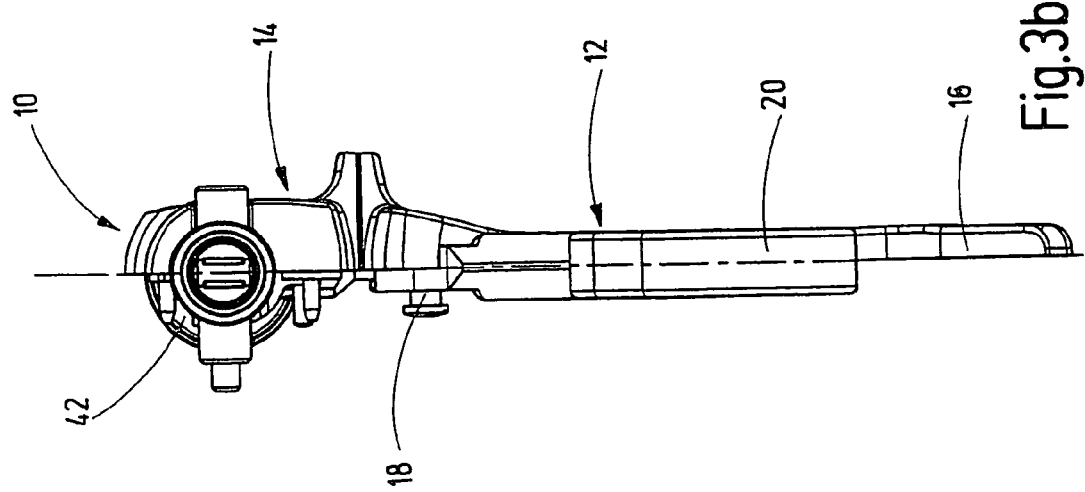
Figure 4A:
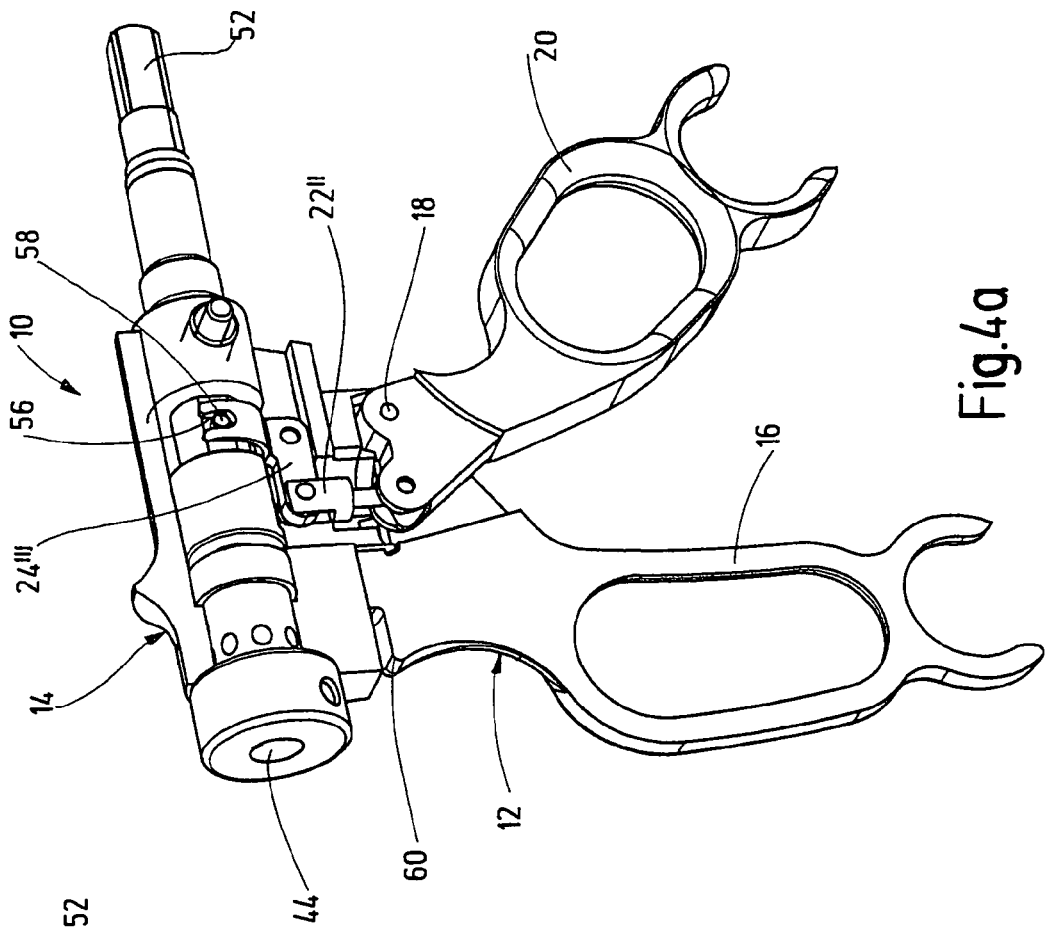
Figure 3D:
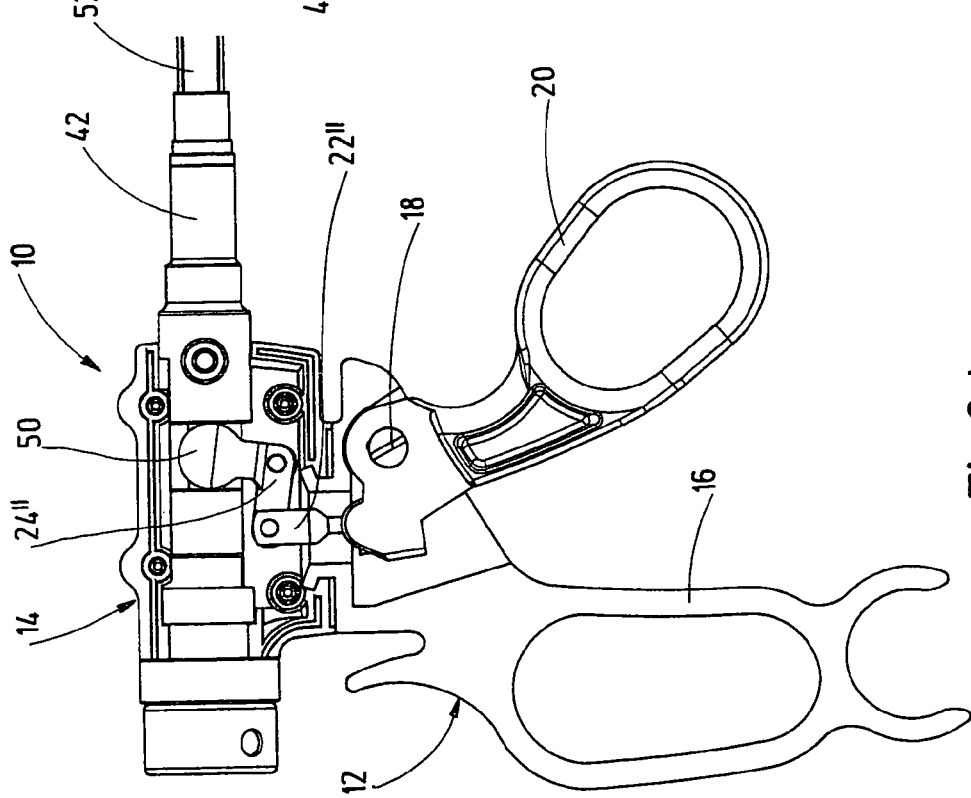
Figure 4C:
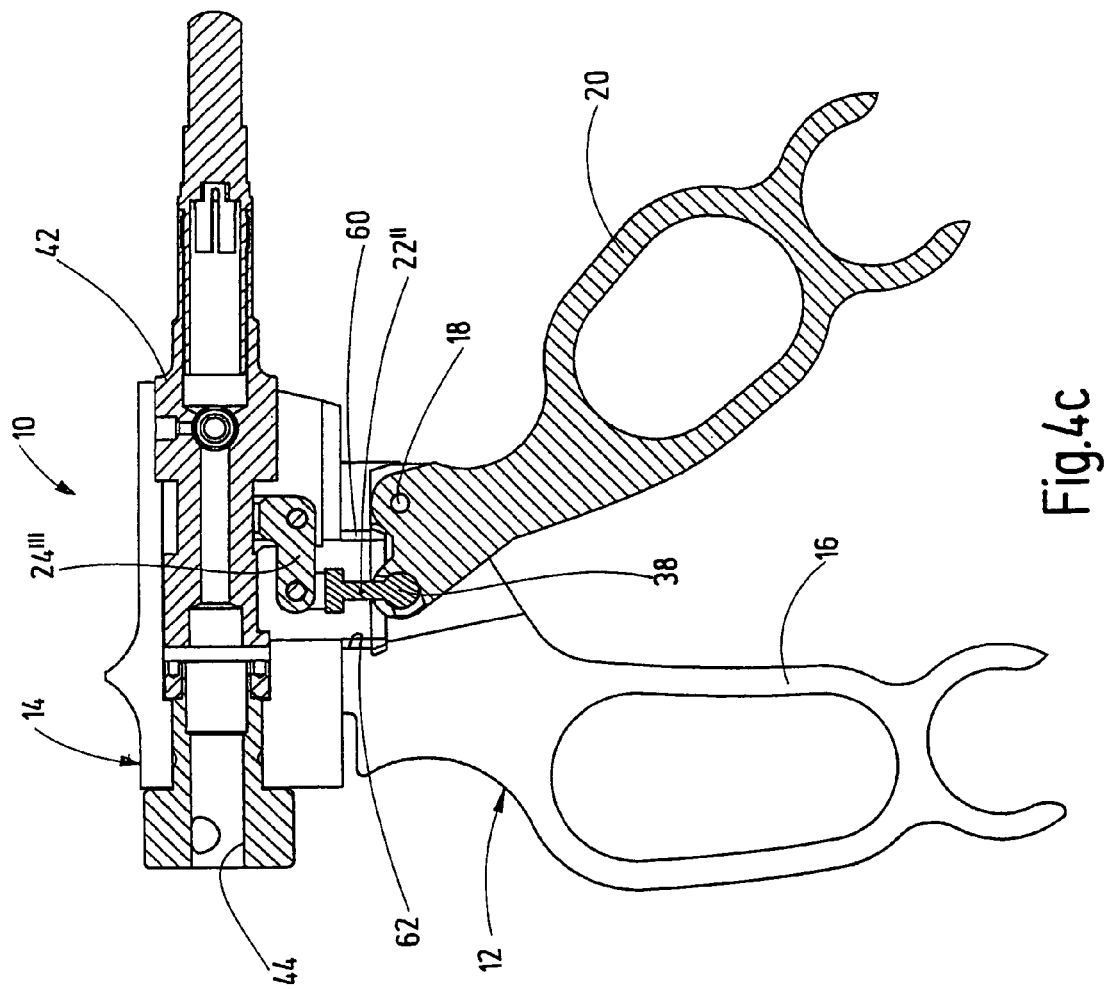
Figure 4B:
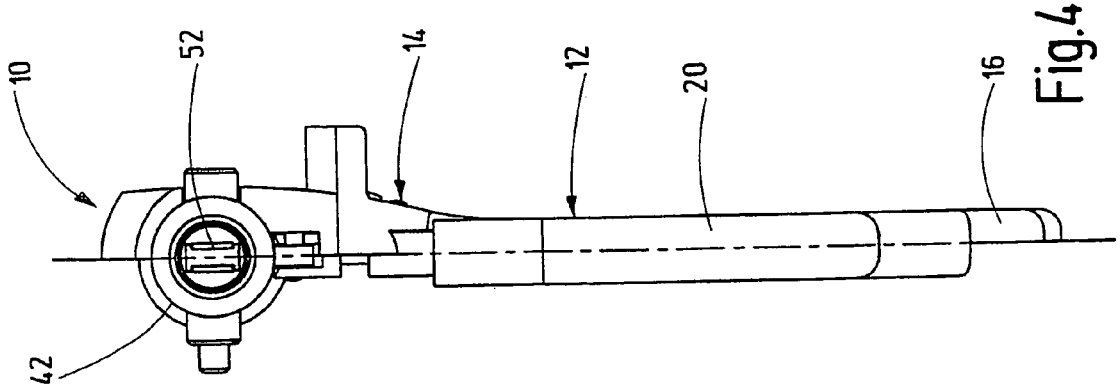

The instrument according to FIGS. 1 and 2 is intended for endoscopic surgery without electrical coagulation.

In the variant according to FIG. 1, the transmission element has a first pair of connecting rods 28 which are mounted with one end in the shaft-receiving element, on both sides of the shaft 26, and whose other ends are articulated pivotably on the free ends of an extension 30 provided on the actuation ram 22 and engaging like a fork around the shaft 26, and a second pair of connecting rods 32 are articulated with one end on the extension of the actuation ram 22, coaxially with respect to the first pair of connecting rods 28, and have their other end articulated pivotably on the shaft 26 acting as actuation member. The lower end of the actuation ram 22 is designed as a ball 38 which is locked in a ball socket 40 of the grip part 20 and secured there. A pivoting of the grip part 20 is thus converted into a sliding movement of the shaft 26.

In the variant according to FIG. 2, the transmission element 24' has substantially the shape of a sector of a circle with a lever extension 34 and is mounted pivotably in the shaft-receiving element 14, with its axis parallel to the pivotable grip part 20, and the outer edge of the transmission element is provided at least partially with teeth 36 which cooperate with complementary teeth on the shaft 26, such that a rack-and-pinion mechanism as it were is created, and the free end of the lever extension 34 is articulated pivotably on the actuation ram 22'.

The instrument according to FIGS. 3 and 4 is designed as a bipolar instrument for endoscopic surgery with optional electrical coagulation. The grip element 12 corresponds to the one shown in FIGS. 1 and 2. However, the shaft-receiving element 14 has, in its axial through-opening, an additional element in the form of a slide piece 42, which itself is intended and designed to receive the actuation member for the tool. The tool shaft with its actuation member is inserted axially into an opening 44 of the slide piece and is locked in the latter as described in DE 10156917 A1. The coupling mechanism here does therefore not act directly on the actuation member but on the slide piece 42. The transmission element 24", 24''' is designed here as a substantially L-shaped lever which, in the area of the connection point of its two arms, is mounted in the shaft-receiving element 14 so as to pivot about an axis 46. The end of one arm is connected pivotably to the actuation ram 22". The second arm is designed like a fork and engages around an actuation part of the slide piece 42.

According to a first variant (FIG. 3), the slide piece 42 has an indent 48 into which approximately circular disk-shaped end portions 50 of the second arm of the transmission element 24" engage. At its proximal end, the slide piece 42 has electrical contacts 52, which can be connected to an external voltage source. The contacts 52 continue into the interior of the slide piece 42 and there form contact points for a shaft that is inserted into the slide piece and that has a tool at its distal end and conductors extending to the tool and with contacts at the proximal end of the shaft.

The grip element 12 has a collar 54 which surrounds the actuation ram 22" and which, with an outwardly angled edge, engages in an opening in the shaft-receiving element 14. The grip element 12 is in this way rotatable relative to the shaft-receiving element 14 about an axis extending in the ram direction, but is connected permanently to the shaft-receiving element 14. The force needed to rotate the two parts 12, 14 relative to each other can be determined by a frictional engagement between the two elements or by an additional shaft ring or spring ring (not shown) that surrounds the collar 54 and is arranged between grip element and shaft-receiving element. The grip element 12 should be able to be rotated relative to the shaft-receiving element 14 without too much force having to be applied, but it should then also remain in the chosen position and should not be moved out of position by the manipulations of the instrument that take place during the operation.

According to another variant (FIG. 4), the end portions of the second arm of the transmission element 24'''' have U-shaped recesses 56 into which pins 58 engage that are arranged laterally on the slide piece 42. The rest of the actuation mechanism corresponds to the one shown in FIG. 3. The rotatable connection between the grip element 12 and the shaft-receiving element 14 is obtained here by means of a locking piece 60 that surrounds the actuation ram and that is integrally molded on the shaft-receiving element 14 and engages in a complementary locking opening 62 in the grip element. Here too, the force needed for rotation can be adjusted by a shaft ring or spring ring that surrounds the locking piece and is arranged between the grip element 12 and the shaft-receiving element 14.

Figure 5:
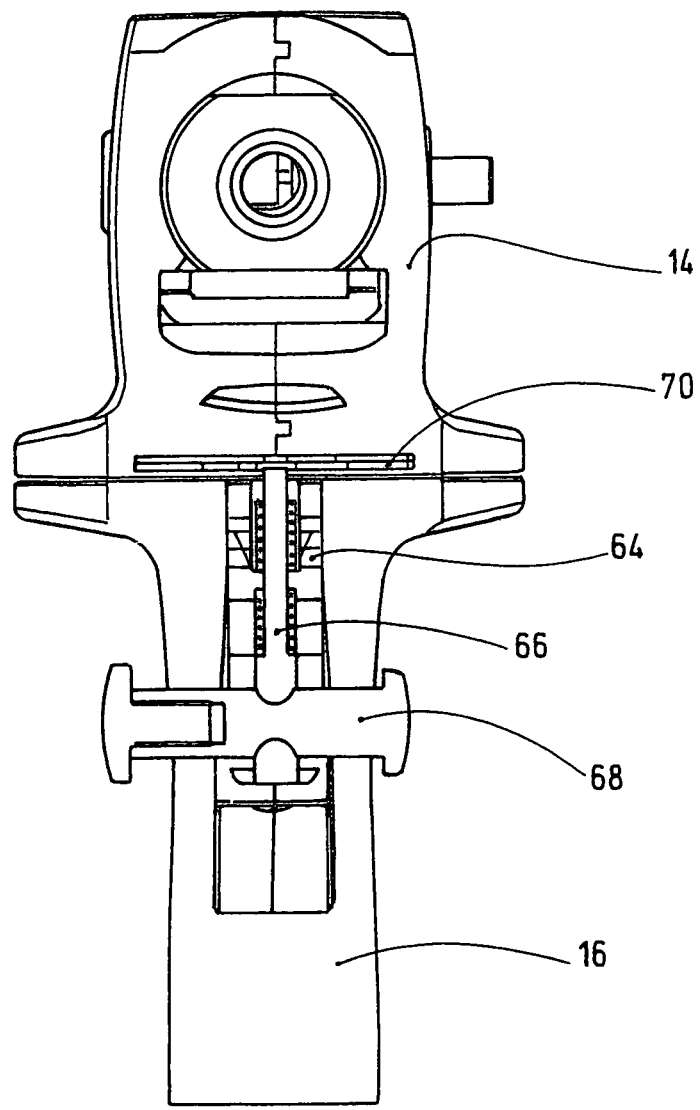
FIG. 5 shows a sectioned front view of another illustrative embodiment of the instrument with a locking mechanism.
Figure 6:
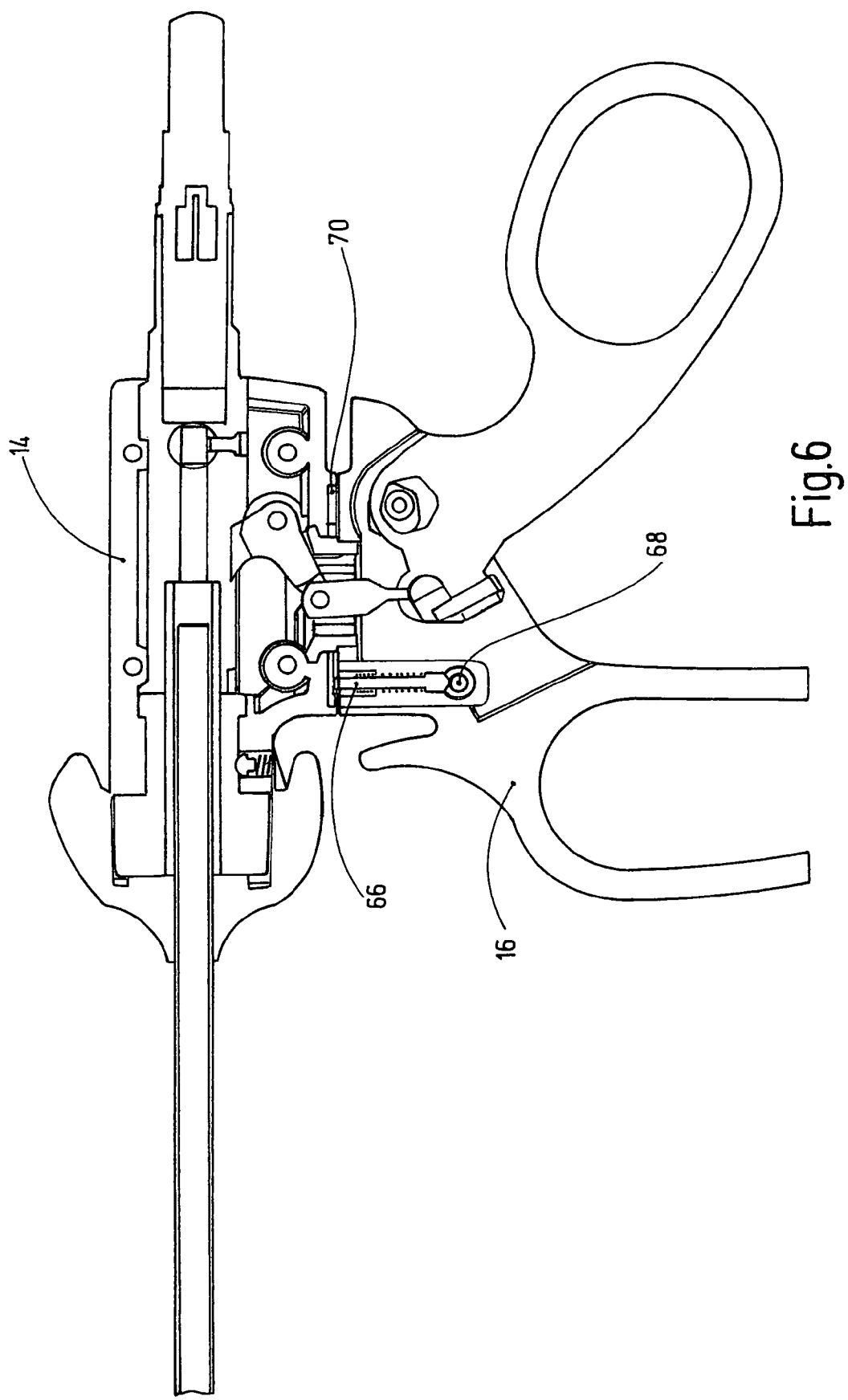
FIG. 6 shows a sectioned side view of the instrument according to FIG. 5.

Another illustrative embodiment (FIGS. 5 and 6) of the instrument has a locking mechanism with which the grip element 12 can be fixed in a desired position of rotation relative to the shaft-receiving element 14. For this purpose, the fixed grip part 16 is provided with a recess 64 which is open toward the shaft-receiving element 14 and in which a spring-loaded locking pin 66 is arranged. By means of an actuation pin 68 extending through the fixed grip part 16, the locking pin 66 is moved between a locking position, in which the grip element 12 is not rotatable relative to the shaft-receiving element 14, and a rotation position, in which the grip element 12 and the shaft-receiving element 14 are rotatable relative to each other. For this purpose, a locking depression is provided in the actuation pin, in which locking depression the locking pin engages in the rotation position. When the actuation pin 68 is moved laterally out of this position, the locking pin 66 is pressed in the direction of the shaft-receiving element 14 where it locks in a locking plate 70 that is fitted for this purpose in the shaft-receiving element and that has locking recesses arranged at defined angle spacings.

The following may be stated in summary: The invention relates to an instrument 10 for endoscopic surgery, with a housing having a grip element 12 and a shaft-receiving element 14, the grip element 12 having a fixed grip part 16 and a pivotable grip part 20, and the shaft-receiving element 14 being intended to receive and lock the proximal end of a tubular shaft 26, with a tool arranged at the distal end of the shaft 26, and with a actuation member being provided for the tool and extending through the shaft and being longitudinally movable therein, or with a slide piece 42 acting on the actuation member, the actuation member engaging with its proximal end in the shaft-receiving element 14 of the housing and being able to be coupled there, via a coupling mechanism arranged in the housing, to the grip part 20 mounted pivotably on the housing, in such a way that a pivoting of the grip part 20 causes a longitudinal movement of the actuation member and an actuation of the tool. In order to allow the operating surgeon to choose a position of his hands in which he can work with the instrument 10 without experiencing fatigue, provision is made according to the invention that the grip element 12 of the housing is rotatable relative to the shaft-receiving element 14 of the housing about a rotation axis extending perpendicular to the shaft 26.

The invention claimed is:

1. Instrument for endoscopic surgery, with a housing having a grip element and a shaft-receiving element, the grip element having a fixed grip part and a pivotable grip part, and the shaft-receiving element being intended to receive and lock the proximal end of a tubular shaft, with a tool arranged at the distal end of the shaft, and with an actuation member being provided for the tool and extending through the shaft and being longitudinally movable therein, or with a slide piece acting on the actuation member, the actuation member engaging with its proximal end in the shaft-receiving element of the housing and being able to be coupled to the grip part mounted pivotably on the housing, in such a way that a pivoting of the grip part causes a longitudinal movement of the actuation member and an actuation of the tool, wherein the grip element of the housing is rotatable relative to the shaft-receiving element of the housing about a rotation axis extending perpendicular to the shaft.

2. Instrument according to claim 1, wherein the pivotable grip part has a ball socket in which a ball head of an actuation ram is mounted.

3. Instrument according to claim 2, wherein the actuation ram is arranged coaxially with respect to the rotation axis of the grip element relative to the shaft-receiving element.

4. Instrument according to claim 2, wherein the actuation ram is coupled to a transmission element for converting the pivoting movement of the pivotable grip part into a sliding movement of the actuation member.

5. Instrument according to claim 4, wherein the transmission element is arranged in the shaft-receiving element of the housing.

6. Instrument according to claim 4, wherein the transmission element has substantially the shape of a sector of a circle with a lever extension and is mounted pivotably in the shaft-receiving element, with its axis parallel to the pivotable grip part, and the outer edge of the transmission element is provided at least partially with teeth which cooperate with complementary teeth on the shaft, and the free end of the lever extension is articulated pivotably on the actuation ram.

7. Instrument according to claim 4, wherein the transmission element has a first pair of connecting rods which are mounted with one end in the shaft-receiving element, on both sides of the shaft, and whose other ends are articulated pivotably on the free ends of an extension provided on the actuation ram and engaging like a fork around the shaft, and a second pair of connecting rods are articulated with one end on the extension of the actuation ram, coaxially with respect to the first pair of connecting rods, and have their other end articulated pivotably on the actuation member.

8. Instrument according to claim 4, wherein the transmission element has a substantially L-shaped pivot lever which is mounted along a pivot axis in the shaft-receiving element and which has one arm coupled pivotably to the actuation ram, while its other arm engages like a fork around the slide piece and is coupled pivotably to the latter.

9. Instrument according to claim 8, wherein the slide piece has, for the purpose of coupling it to the transmission element, two laterally protruding pins which engage in U-shaped recesses in the free ends of the fork-like arm of the transmission element.

10. Instrument according to claim 8, wherein, for the purpose of coupling it to the transmission element, the slide piece has, at least in its lateral area, recesses or a peripheral indent in which circular end portions of the fork-like arm of the transmission element engage.

11. Instrument according to claim 1, wherein a shaft ring or spring ring is arranged, coaxially with respect to the rotation axis, between the grip element and the shaft-receiving element.

12. Instrument according to claim 1, wherein an electrical alternating voltage is applied to the tool for electro-surgical treatment of tissue.

13. Instrument according to claim 12, wherein electrical contacts for attachment of a voltage source are provided in the proximal area of the slide piece, and the contacts are connected to the tool via conductors that are routed in an electrically insulated manner through the shaft.

14. Instrument according to claim 1, wherein a spring-loaded locking pin is provided in the fixed grip part and is movable, relative to the shaft-receiving element, between a locking position, in which the grip element is not rotatable relative to the shaft-receiving element, and a rotation position, in which the grip element and the shaft-receiving element are rotatable relative to each other.

15. Instrument according to claim 14, wherein a locking plate lying opposite the locking pin in the fixed grip part is arranged in the shaft-receiving element, into which locking plate the locking pin can engage at predetermined angle spacings.

* * * * *